Figure 1:
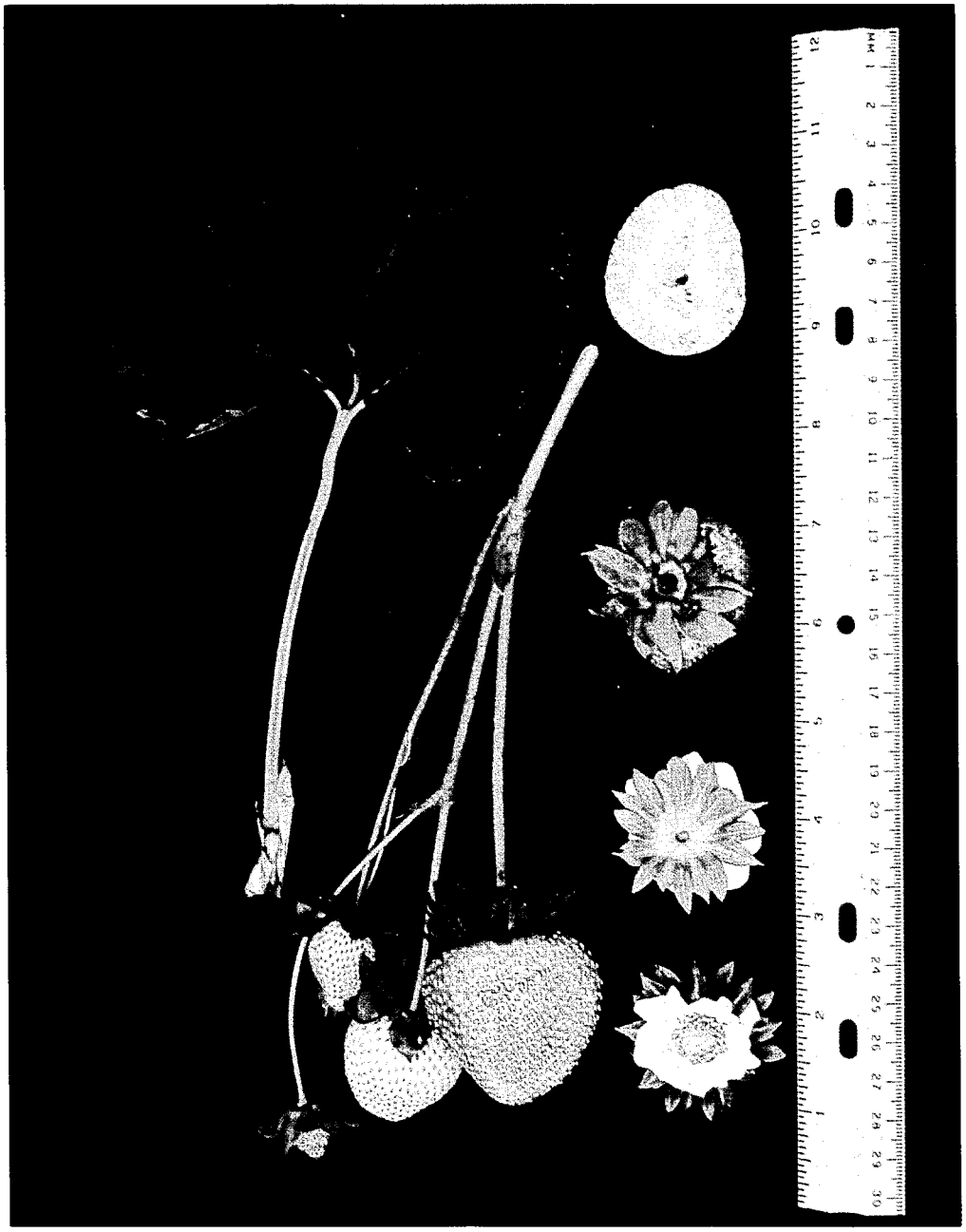

United States Patent [19]

Johnson, Jr.

[11] Plant 3,987

[45] Dec. 14, 1976

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 637,790

[22] Filed: Dec. 4, 1975

[51] Int. Cl.[2] ..... A01H 5/03

[52] U.S. Cl. ..... Plt./49

[58] Field of Search ..... Plt./49, 48

*Primary Examiner*—Robert E. Bagwill

EXEMPLARY CLAIM

1. The new and distinct variety of strawberry plant herein described and illustrated, and identified by the characteristics enumerated above.

1 Drawing Figure

STRAWBERRY PLANT

This invention relates to a new and distinct variety of strawberry plant known as H4 and which is the result of a cross of the unpatented variety known as The Driscoll Strawberry Associates Selection Y5 and The Driscoll Strawberry Associates Selection D9.

The seedlings resulting from the aforementioned cross were grown and asexually multiplied in Shasta County, Calif., and tested in the fruiting beds on the property of member growers of Driscoll Strawberry Associates, Inc. Clones of the seedlings were also held at the Propagation Nursery in Shasta County. One plant was selected from the aforementioned group of seedlings and further asexually reproduced in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

FIG. 1 of the accompanying drawing illustrates plant parts of the new variety, typical in size, shape and color.

A berry in cross section illustrates flesh color and characteristic core cavity. The inflorescence pictured illustrates typical branching and relative size during May and June. The pedicel holding the primary berry originates mainly at the axil union of two secondary peduncles, as is shown in the illustration, with a smaller percentage originating from one of the secondary peduncles. The drawing also illustrates long pedicels with just two secondary peduncles, which is the most common number per inflorescence. The common peduncle is considered long, often longer than the one illustrated. The large showy calyx is typical, as is the large diameter and over-lapping sepals. The medium conic to slightly wedge shaped fruit is typical, as is the abundance of exerted seed which gives the fruit firmness. The berry in cross section shows a typical core and color. The flower shows typical petals and mature anthers that normally produce an abundance of pollen. The dark leaflets that are cupped upward are typical, as is the petiole which is normally free of bracts. The petiolule of the central leaflet is conspicuous in the picture and is a typical length.

This novel new summer planted, spring variety is adapted mainly to use in Southern California, even though it is productive in the central coast regions of California. The new variety will also produce well when winter planted and mulched with polyethylene, a common practice in Southern California. If winter planted in Southern California, Ventura County, fruiting from the crown crop usually will ripen during mid-March; if summer planted, mid-April. The plant of this variety is medium in size, but is larger than Driscoll G6, U.S. Plant Pat. No. 3473. The leaflets and foliage are normally darker and larger and the petiole and petiolules are also longer than the G6. The inflorescence of the new variety is generally larger, especially the common peduncle with the flowers more visible above the plant than G6. The pedicel holding the primary berry more often originates at the axil formed by the union of secondary peduncles than does G6. The berry size of G6 is consistently larger and the crop more uniform in its production over the total fruiting season. The fruit, however, is firmer, darker and the seed more exerted on the new variety. The calyx is larger and individual sepals are larger and more abundant, as well as noticeable on the new variety than G6. The fruit shape of the new variety is less globose, but more irregular than G6. The shoulders of the fruit near the calyx are round, not necked, but they are not as rounded as the G6 variety. The size variation between primary and secondary berries is greater on the new variety. The new variety generally ripens only one berry on an inflorescence at a time in contrast to two or three by G6. The fruit colors more consistently on the new variety and is not as susceptible to albino coloring (or lack of red pigment) of the fruit, a condition common to the G6. This condition is described in Strawberry Scientific literature and occurs when plants are given an excessive amount of nitrogen during periods of low light intensity. The G6 is sweeter and more flavorful to the taste, but is lower in ascorbic acid than the new variety. The aroma of fruit from the new variety is equal to that of G6. The new variety is equal to G6 in its susceptibility to the two-spotted mite and mildew, but it is more susceptible to the Mycosphaerella Leafspot. The new variety is a more prolific runner producer both at the nursery and the fruiting beds, but the runner plants from the nursery are generally not as large as the G6.

As a seedling and selection, this new variety withstood the natural invasions of certain virus components found in Central California without losing its ability to produce.

The varietal characteristics of the novel plant, described below in detail, were observed mainly during the first fruiting season, but reference is also made to the appearance during the second fruiting year. Observations were made in the Watsonville area of California, which is a cool coastal area near the Pacific Ocean. The drawing was taken in Watsonville on May 30, and the specific measurements were made during late spring and summer in Watsonville, Calif. The color terminology as used herein is in accordance with Ridgeways Color Standards and Nomenclature (1912 Edition).

Plants: Medium to large, vigorous if given ample nutrients and kept free of the two-spotted mite and Mycosphaerella Leafspot. It has an extensive root system.

Leaflets: Medium to large in size, central leaflet is mostly 7 to 10 cm. in length and width, but may vary, depending on the environment and time of year. If during peak production and under stress, leaflet size may be reduced. Petiole length also varies, depending on the environment, but are mostly 15 to 20 cm. during July, when measuring from base of petiole in crown to petiolule. Petiolules of central leaflets are considered medium to long, mostly 8 to 12 mm. Serrations at margin of leaflets are medium deep, abundant, ovate with an acute apex, often double. Bracts are not normally present on the petiole. The leaflet surface is mildly rugose with a slight puffiness appearing between the small veins of the leaflets of vigorously growing leaflets and there is an irregular cupping upward at the margins. The color of the upper side of the leaflet is Yew Green, Plate XXXI.

Runners: Runners are vigorous and abundant, both at the nursery and the fruiting bed.

Inflorescence: Medium to long in length, mostly 20 to 25 cm. during mid-summer period. The common peduncle is medium in length but varies, mostly 5 to 15 cm. usually only two secondaries per inflorescence. Primary and secondary berries ripen independently of each other, usually only one berry ripe on inflorescence at a time. Pedicel holding primary berry usually originates at the axil of the peduncles, but may originate from one of the peduncles (see FIG. 1). Flowers are medium to large in size, producing anthers with an abundance of pollen even in early spring. Flowers visible above the plant during heavy crop period, especially spring crop. Hair on pedicles holding primary berries 20 mm. from the berry, irregularly parallel to the pedicel.

Fruit: The first crop of berries produced during the spring after a summer planting are medium to large if the plant growth is adequate to support the large crop. Subsequent crops are smaller with secondary and tertiary berries dropping off in size. Primary berries during May and June, 40 to 45 mm. in length with the width equal to the length. Fruit shape is mainly medium conic to medium wedge with secondary and tertiaries globose conic to globose wedge, as described in the USDA Bulletin 1043. Primaries show considerable variation in shape and may produce irregular longitudinal folds or ribs. Shoulders of the fruit near calyx are rounded, not necked. Except for the first berries in spring, the fruit colors consistently. Seed generally yellow, but may darken when exposed to direct sunlight. The seed is generally held equal to or exerted at the surface which usually gives the fruit firmness, but may distract from the appearance at times. The core is medium in size, but tight. The flesh is firm, but often lacks moisture when biting into the fruit and along with low sweetness gives to the variety a poor to medium dessert quality. Color of fruit surface is Carmine, Plate I, and the flesh color is Scarlet Red, Plate I, near the epidermis and Peach Red, Plate I, at the core. The ascorbic acid content of the fresh fruit is high, 90 mg. per 100 gms. fruit during May.

Calyx: Medium to large in diameter in relationship to fruit size, mostly 40 to 45 mm. in diameter on primaries. Sepals mainly 14 to 16 in number. Many sepals may overlap and may become serrated and are mostly ovate and short acute in outline. Some calyx may be clasping, but some may be reflexed. The color of sepals on the side facing the fruit is light Cress Green, Plate XXXI, becoming Cress Green, Plate XXXI, next to fruit.

I claim:

1. The new and distinct variety of strawberry plant herein described and illustrated, and identified by the characteristics enumerated above.

* * * * *